US 6,358,238 B1

(12) United States Patent
Sherry

(10) Patent No.: US 6,358,238 B1
(45) Date of Patent: Mar. 19, 2002

(54) EXPANDABLE MICRO-CATHETER

(75) Inventor: John Sherry, Needham, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/388,565

(22) Filed: Sep. 2, 1999

(51) Int. Cl.⁷ .......................................... A61M 25/00
(52) U.S. Cl. ................................................. 604/524
(58) Field of Search ............................. 604/264, 523, 604/524, 526, 527, 536, 535, 104, 105, 106, 107, 108, 109

(56) References Cited

U.S. PATENT DOCUMENTS

| | | | |
|---|---|---|---|
| 3,788,318 A | 1/1974 | Kim et al. ............... 128/214.4 |
| 4,406,656 A | 9/1983 | Hattler et al. ............... 604/280 |
| 4,610,671 A | 9/1986 | Luther .......................... 604/168 |
| 4,668,221 A | 5/1987 | Luther .......................... 604/164 |
| 4,995,872 A | 2/1991 | Ferrara ........................ 604/280 |
| 5,061,254 A | 10/1991 | Karakelle et al. ........... 604/265 |
| 5,066,285 A | 11/1991 | Hillstead .................... 604/164 |
| 5,102,401 A | 4/1992 | Lambert et al. ............. 604/264 |
| 5,106,368 A | 4/1992 | Uldall et al. .................. 604/43 |
| 5,159,050 A | 10/1992 | Onwumere .................. 528/67 |
| 5,176,659 A | 1/1993 | Mancini ...................... 604/280 |
| 5,246,424 A | 9/1993 | Wilk ............................ 604/164 |
| 5,318,588 A | 6/1994 | Horzewski et al. ......... 606/198 |
| 5,324,262 A | 6/1994 | Fischell et al. ............... 604/96 |
| 5,407,430 A | 4/1995 | Peters .......................... 604/104 |
| 5,447,503 A | 9/1995 | Miller ......................... 604/280 |
| 5,454,790 A | 10/1995 | Dubrul ........................ 604/104 |
| 5,533,968 A | 7/1996 | Muni et al. .................... 604/96 |
| 5,573,508 A | 11/1996 | Thornton ...................... 604/96 |
| 5,573,509 A | 11/1996 | Thornton ..................... 604/102 |
| 5,618,267 A | 4/1997 | Palestrant ..................... 604/53 |
| 5,647,358 A | 7/1997 | Vilasi .......................... 128/207 |
| 5,766,201 A | 6/1998 | Ravenscroft et al. ....... 606/194 |
| 5,814,058 A | 9/1998 | Carlson et al. ............. 606/185 |
| 5,827,227 A | 10/1998 | DeLago ....................... 604/104 |
| 5,911,702 A | 6/1999 | Romley et al. ............... 604/53 |
| 5,935,122 A | 8/1999 | Fourkas et al. ............. 604/523 |

FOREIGN PATENT DOCUMENTS

EP         0 839 549 A1    6/1998

*Primary Examiner*—Manuel Mendez
(74) *Attorney, Agent, or Firm*—Crompton, Seager & Tufte, LLC

(57) ABSTRACT

A catheter and method for delivering a therapeutic agent (e.g., an embolic material) to a vascular site. The intravascular catheter is navigated, at a first relatively small diameter, to the vascular site. Pressure is applied to the lumen of the shaft, thereby expanding an expandable portion of the catheter shaft from the first diameter to a second larger diameter, suitable for delivery of a therapeutic agent. The therapeutic agent is preferably disposed in the lumen of the shaft such that the expansion pressure is created, in part, by resistance of the therapeutic agent to flow through the lumen. Preferably, the shaft expands predictably with pressure. A reinforcement structure may be utilized in the shaft of the catheter, including the expandable portion. The reinforcement structure may include a plurality of circumferential elements, each circumferential element having a circumference and a means for permitting an increase in the circumference such that the shaft is able to expand.

36 Claims, 5 Drawing Sheets

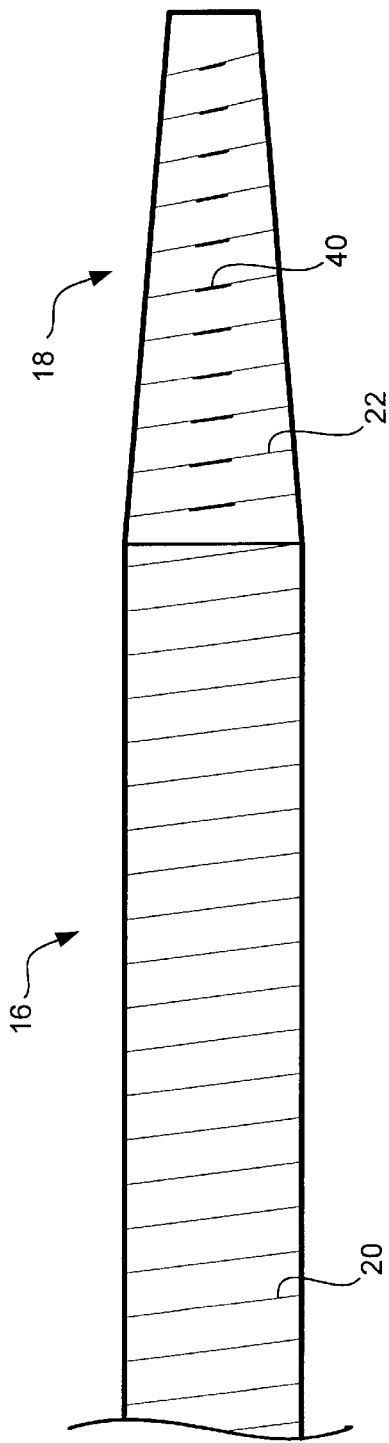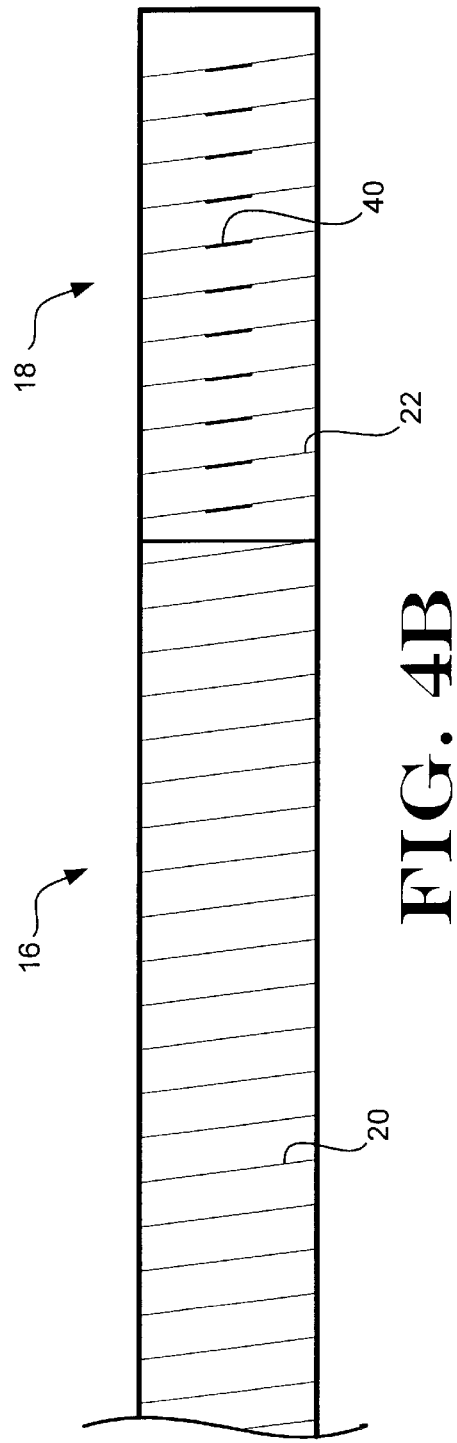

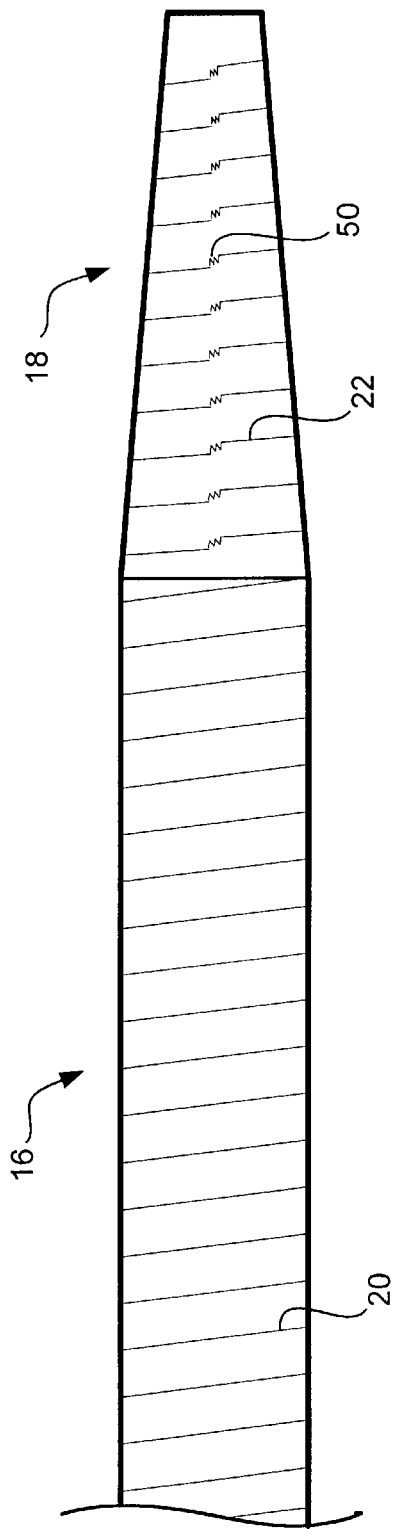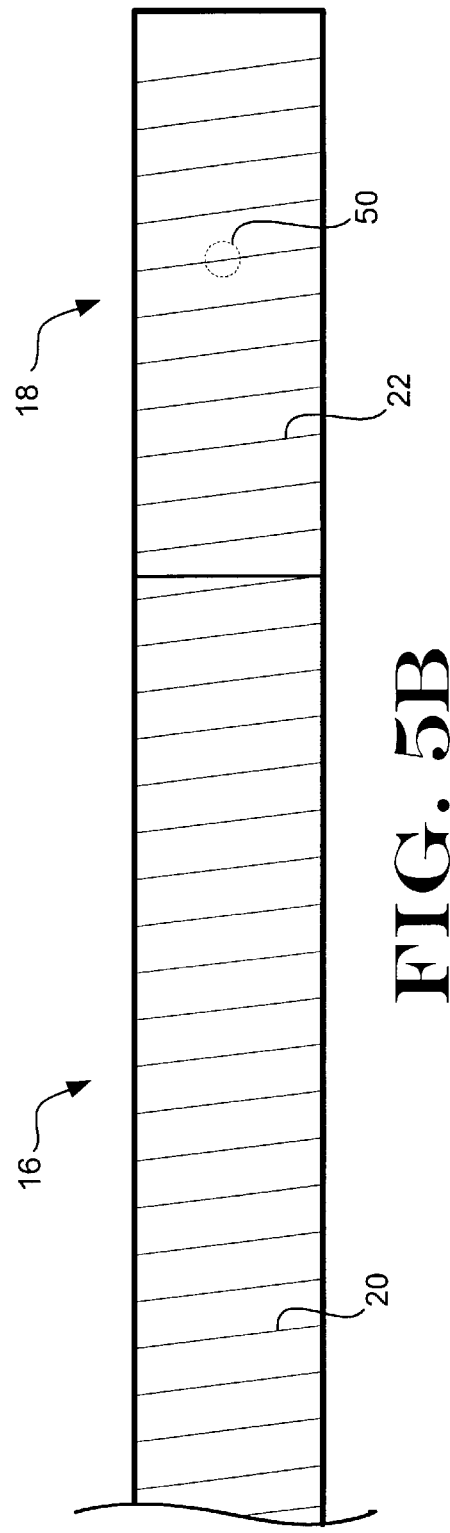
FIG. 5A
FIG. 5B

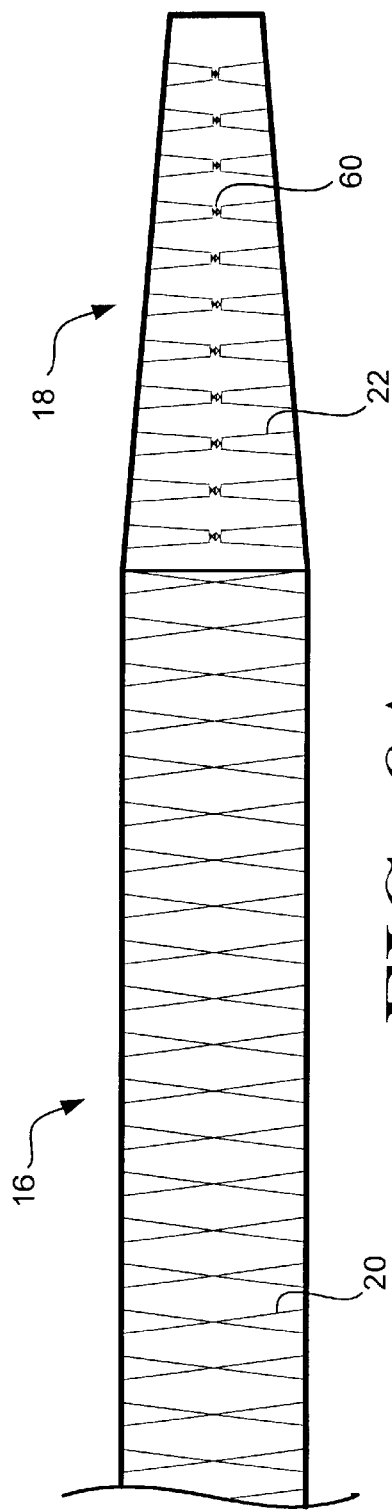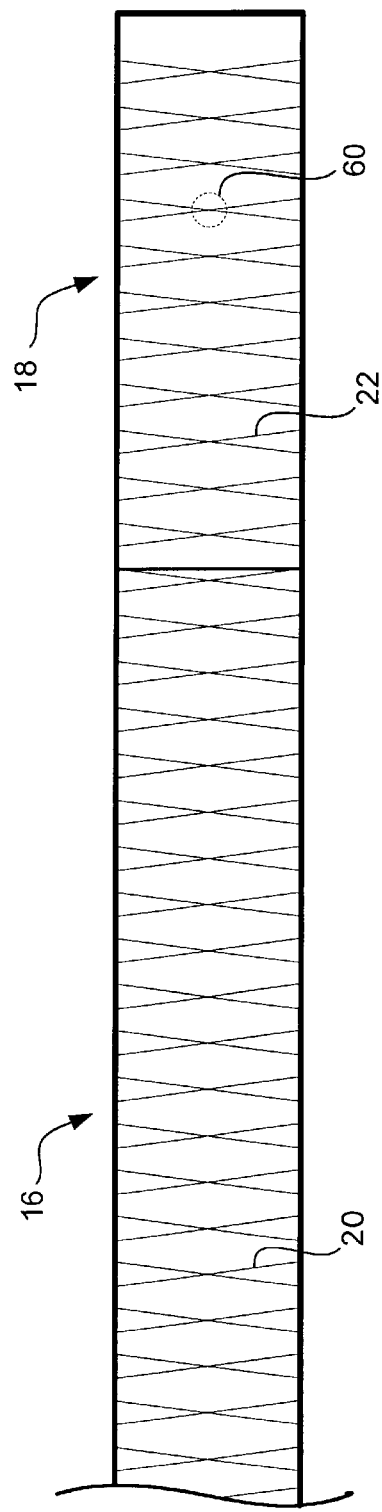

EXPANDABLE MICRO-CATHETER

FIELD OF THE INVENTION

The present invention generally relates to intravascular catheters. More specifically, the present invention relates to low profile intravascular micro-catheters.

BACKGROUND OF THE INVENTION

Intravascular catheters are used in a wide variety of relatively non-invasive medical procedures. Such intravascular catheters may be used for diagnostic or therapeutic purposes. Generally, an intravascular catheter allows a physician to remotely perform a medical procedure by inserting the catheter at a location that is easily accessible and thereafter navigating the catheter to the desired target site. By this method, virtually any target site in the patient's vascular system may be remotely accessed, including the coronary, cerebral, and peripheral vasculature.

Intravascular catheters typically have a radiopaque portion and are guided through the patient's vascular system with the assistance of x-ray fluoroscopy. A physician may manipulate the proximal end of the catheter and fluoroscopically monitor the corresponding movement of the distal end of the catheter. Thus, it is desirable that the catheter be sufficiently radiopaque along its length and particularly at its distal end to enable the physician to clearly monitor the progress of the catheter as it is being advanced from the vascular access site to the vascular target site.

After the intravascular catheter has been navigated through the patient's vascular system with the distal end thereof adjacent the target site, the catheter may be used for various diagnostic and/or therapeutic purposes. Frequently, diagnostic and therapeutic techniques require the infusion of fluids or other materials through the catheter. For example, it may be desirable to deliver an embolic material (e.g., embolic gel, coil, etc.) through the catheter to embolize an aneurysm, shunt, or the like, inject radiopaque contrast media through the catheter to provide enhanced fluoroscopic visualization for diagnostic purposes, or inject pharmaceutical solutions (i.e., drugs) to the target site for therapeutic purposes. In order to maintain a fluid path in the catheter for such purposes, it is desirable that the catheter be sufficiently resistant to kinking. In addition, because such fluids are typically delivered under pressure, it is also desirable that the catheter be sufficiently resistant to bursting.

To satisfy some of these desirable features, prior art intravascular catheters have utilized a reinforcement structure such as a braid or coil disposed between an inner lubricious tubular layer and an outer flexible tubular layer. A braid reinforcement structure offers high resistance to bursting, and a coil reinforcement structure offers resistance to ovaling and kinking. Thus, an intravascular catheter may be kink resistant or burst resistant by utilizing a reinforcement structure such as a coil or braid.

It is also desirable that an intravascular catheter be relatively long and flexible because the distance between the access site and the target site is often in excess of 100 cm and is usually defined by a tortuous path. In addition, because the inside diameter of the vasculature at the target site is often less than 5 mm, it is also desirable that the intravascular catheter have a small profile. Accordingly, an intravascular catheter is preferably long, flexible, and thin.

To provide a relatively thin or small profile catheter, various collapsible and expandable shaft designs have been proposed. However, these designs are not suitable for the delivery of embolic material to remote target sites. Further, these designs do not offer a reinforcement structure in the expandable portion, which may compromise kink resistance and burst resistance as described previously. Examples of such prior art catheters may be found in U.S. Pat. No. 4,406,656 to Hattler et al., U.S. Pat. No. 5,618,267 to Palestrant, and U.S. Pat. No. 5,318,588 to Horzewski et al.

U.S. Pat. No. 4,406,656 to Hattler et al. discloses a venous catheter including a plurality of collapsible lumens formed from a material which is normally collapsed in a small cross-sectional area and which is further capable of expanding when fluid is flowing therein to a cross-sectional area which is much greater than that when collapsed. Each of the collapsible lumens defines a fluid passageway for the infusion of fluid therethrough. The sides of the collapsible lumen are made from a material having sufficient resiliency to expand outwardly as fluid flows through the passageway.

U.S. Pat. No. 5,618,267 to Palestrant discloses a collapsible infusion catheter formed of a normally flattened tube of flexible, collapsible plastic. The infusion catheter is initially in a collapsed configuration. During infusion, the catheter expands to a generally oval profile. The infusion catheter allegedly reduces the likelihood of clot formation, minimizes blood flow obstruction when the catheter is collapsed, and provides an expanded flow lumen for infusing fluids.

U.S. Pat. No. 5,318,588 to Horzewski et al. discloses a radially expandable intravascular catheter formed of an elastic material. The intravascular catheter may be expanded in the radial direction by inserting a diagnostic, therapeutic, or other device into the catheter lumen. With this arrangement, the catheter lumen is expanded by radial forces applied by physical contact with the device inserted into the lumen.

Among other deficiencies, none of these proposed catheter designs are particularly suitable for the delivery of embolic material to remote target sites. Further, none of these proposed catheter designs offer reinforced expandable portions.

SUMMARY OF THE INVENTION

The present invention overcomes these disadvantages by providing a method of delivering a therapeutic agent (e.g., an embolic material) to a vascular site using a catheter including a shaft having an expandable portion, preferably with a reinforcement structure. The catheter is navigated, at a first relatively small diameter, to the vascular site. Pressure is applied to the lumen of the shaft thereby expanding the expandable portion of the shaft from the first diameter to a second larger diameter, suitable for delivery of a therapeutic agent. The therapeutic agent is then delivered to the vascular site through the lumen of the catheter. The therapeutic agent is preferably disposed in the lumen of the shaft such that the expansion pressure is created, in part, by resistance of the therapeutic agent to flow through the lumen.

Preferably, the shaft expands predictably with pressure. For example, the first diameter may be maintained below a first threshold pressure. The second diameter may be established at a second threshold pressure and maintained above the second threshold pressure.

The present invention also provides an intravascular catheter having a reinforced tubular shaft, at least a portion of which is expandable. The shaft includes a lumen extending therethrough and an open distal end. The expandable portion is sufficiently expandable such that the shaft may expand from a first diameter to a second diameter upon increasing the pressure in the lumen of the shaft. Preferably, the expandable portion is sufficiently elastic such that the shaft may return to the first diameter upon decreasing the pressure in the lumen of the shaft. The expandable portion may be disposed at the distal end of the shaft, preferably in the form of a tapered tip.

The reinforcement structure may comprise, for example, a coil, a braid, a knit or an intermediate tube. In any instance, the reinforcement structure includes a plurality of circumferential elements having means for permitting an increase in the circumference. The circumference-increasing means may comprise, for example, a spring, an elastic segment, or slack in the circumferential element.

The reinforcement structure within the expandable portion may be disposed on or in a polymer tubular layer, or between two polymer tubular layers. The polymer layers are also sufficiently expandable to permit expansion of the shaft. Preferably, the polymer layer or layers permit relative movement of the circumference-increasing means. By permitting an increase in circumference, the reinforcement structure allows the shaft to expand from the first diameter to the second diameter.

BRIEF DESCRIPTION OF THE DRAWINGS

FIG. 4A is a detailed view of a first embodiment of the distal portion of the catheter illustrated in FIG. 1, shown in the collapsed position;

FIG. 4B is a detailed view of the distal portion illustrated in FIG. 4A, shown in the expanded position;

FIG. 5A is a detailed view of an alternative embodiment of the distal portion of the catheter illustrated in FIG. 1, shown in the collapsed position;

FIG. 5B is a detailed view of the distal portion illustrated in FIG. 5A, shown in the expanded position;

FIG. 6A is a detailed view of another alternative embodiment of the distal portion of the catheter illustrated in FIG. 1, shown in the collapsed position;

FIG. 6B is a detailed view of the distal portion illustrated in FIG. 6A, shown in the expanded position.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
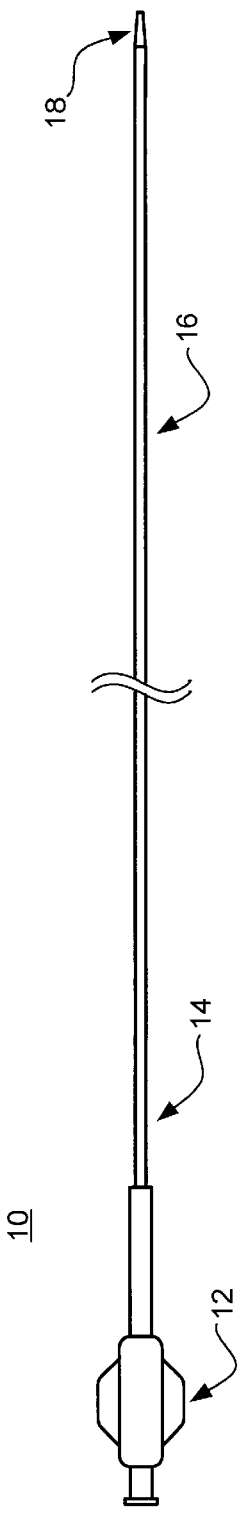
FIG. 1 is a plan view of an intravascular catheter in accordance with one embodiment of the present invention.
Figure 2:
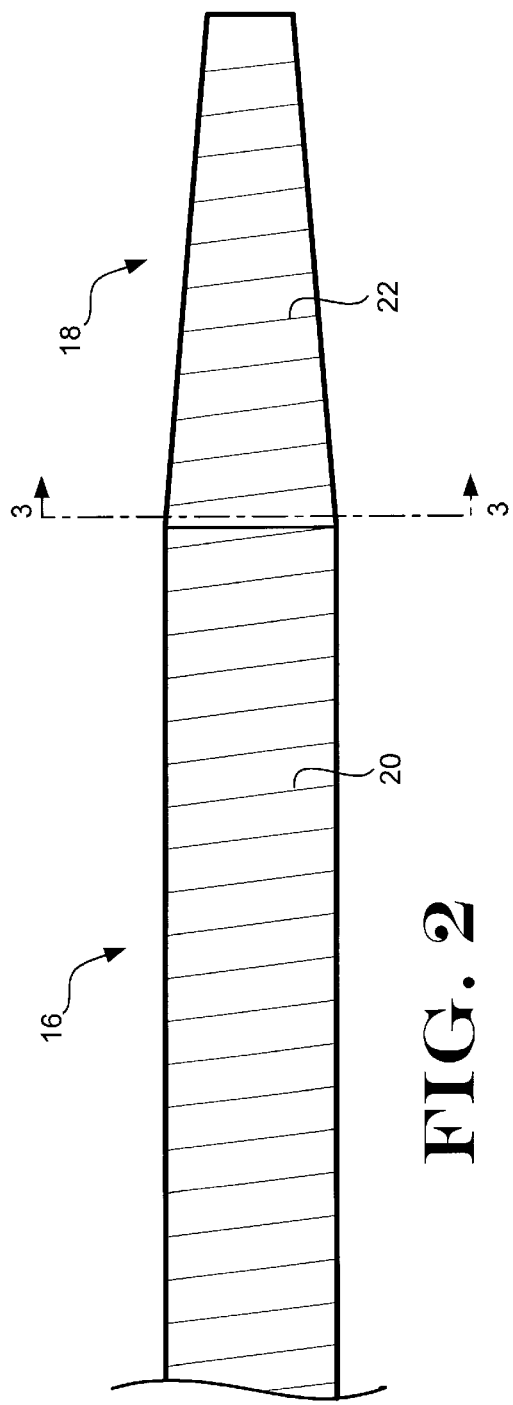
FIG. 2 is a detailed view of a distal portion of the catheter illustrated in FIG. 1.
Figure 3:
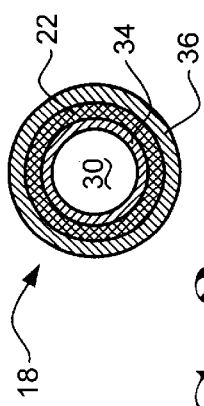
FIG. 3 is a cross-sectional view taken along line 3—3 in FIG. 2.

Refer now to FIGS. 1–3, which illustrate an intravascular catheter 10 in accordance with one embodiment of the present invention. Intravascular catheter 10 includes a manifold 12 connected to the proximal end of a proximal shaft portion 14. The distal end of the proximal shaft portion 14 is connected to the proximal end of a distal shaft portion 16. The distal end of the distal shaft portion 16 is connected to a distal tip 18, which may be tapered (as shown) or may be uniform in diameter. The proximal shaft portion 14, distal shaft portion 16, and distal tip portion 18 may be integrally formed or may be formed by joining a plurality of individual tubular segments. At least one lumen 30 extends through each of the shaft portions 14, 16, 18 to define a fluid path extending from the proximal end of the manifold 12 to the distal end of the distal tip portion 18. The distal end of the distal tip portion 18 is open such that fluid or other materials introduced into the catheter 10 may be delivered to the desired treatment site via lumen 30.

Refer now to FIG. 2, which illustrates a detailed view of the distal shaft portion 16 and the distal tip portion 18. In this particular embodiment, the distal tip portion 18 is expandable from a first diameter (shown) approximating a tapered profile to a second diameter (not shown) approximating a nominal diameter of the distal shaft portion 16. Alternatively, the first diameter may approximate the nominal diameter of the distal shaft portion 16 and the second diameter may approximate an enlarged profile.

It may be desirable, in some instances, to render the distal shaft portion 16 expandable in addition to the distal tip portion 18. In other instances, it may be desirable to render the proximal 14 and the distal 16 shaft portions expandable in addition to the distal tip portion 18. For purposes of simplicity and illustration only, the present invention is described with reference to an expandable distal tip portion 18, wherein the proximal 14 and the distal 16 shaft portions are not expandable.

The first (collapsed) diameter allows the catheter 10 to be easily navigated through tortuous vasculature to access a remote target site. The second (expanded) diameter allows for the delivery of a therapeutic fluid or other material, such as an embolic material. Such fluid or material may be delivered by generating a pressure inside the lumen 30. This pressure may also be used to expand the distal tip portion 18 from the first diameter to the second diameter. Pressure inside the lumen 30 is generated by connecting a pressurized fluid source (e.g., a syringe) to the manifold 12. The fluid or other material resists flow through the lumen 30 and thereby assists in generating pressure inside the lumen 30.

Catheter 10 preferably includes a reinforcement structure 20 such as a coil, a braid, a knit or an intermediate flexible tube. Each of these specific reinforcement structures 20 have a plurality of circumferential elements. For example, each circumferential element of the coil is a circumferential element. Similarly, since a braid is a plurality of interwoven coils, each circumferential element of each coil in the braid is a circumferential element. As applied to the knit wherein a plurality of fibers are knit in a tubular shape but no single fiber traverses the entire circumference, a circumferential element may be defined as the set of fibers that form a complete circumferential element about the circumference of the tube. As applied to an intermediate flexible tube, a circumferential element may be defined as a band of material that forms a complete circumferential element about the circumference of the tube.

An expandable reinforcement structure 22 is disposed in the expandable distal tip portion 18 of the catheter 10. The reinforcement structure 20 disposed in the proximal shaft portion 14 and the reinforcement structure 22 disposed in the distal shaft portion 16 differ only in that the expandable reinforcement structure 22 permits radial expansion of the distal tip portion 18 upon the application of pressure inside the lumen 30 of the catheter 10. The expandable reinforcement structure 22 may comprise a coil, a braid, a knit or an intermediate tube, each of which have a plurality of circumferential elements.

Expandable reinforcement structure 22 allows expansion by providing a means 40, 50, 60 (shown in FIGS. 4–6) for allowing an increase in the circumference of the individual circumferential elements of the reinforcement structure 22. Specifically, as the expandable portion increases from the first diameter to the second diameter, the circumference of the individual circumferential elements increase proportionally. The increase in circumference may be accommodated by, for example, an elastic segment, a spring, or slack in each circumferential element. Each of these means for allowing an increase in the circumference of each circumferential elements is described in more detail with reference to FIGS. 4–6.

Refer now to FIG. 3, which illustrates a cross-sectional view of the expandable distal tip portion 18 taken along line 3—3 in FIG. 2. In this particular embodiment, the expandable reinforcement structure 22 is disposed between an inner layer 34 and an outer layer 36. Inner layer 34 preferably comprises a lubricious polymer such as PTFE or FEP, and outer layer 36 is preferably formed of a flexible polymer such as a nylon copolymer or the like. Although not illustrated, the proximal portion 14 and the distal portion 16 of the shaft are similarly constructed with reinforcement structure 20 using known manufacturing techniques. Reinforcement structures 20 and 22 may be disposed between two polymer layers 34, 36 as illustrated. Alternatively, the reinforcement structures 20 and 22 may be disposed in or on a single polymer layer. Reinforcement structures 20 and 22 may be formed of polymeric materials such as LCP or metallic materials such as SST or NITI, or may be formed of a combination of polymeric and metallic materials, particularly when a plurality of coils or a braid are utilized.

Refer now to FIGS. 4A and 4B, which illustrate a detailed view of a first embodiment of the distal tip portion 18 of the catheter 10 illustrated in FIG. 1, shown in the collapsed position and expanded position, respectively. In this particular embodiment, each circumferential element of the reinforcement structure 22 includes an elastic segment 40. Elastic segment 40 permits each circumferential element of the reinforcement structure 22 to increase in circumference, thereby allowing the distal tip portion 18 to expand radially. Elastic segment 40 may be formed of the same or different material as used for the remaining portions of the reinforcement structure 22. Although each circumferential element of the reinforcement structure 22 is illustrated as having an elastic segment 40, it should be understood that any number of the circumferential elements of the reinforcement structure 22 may include element 40. Furthermore, each circumferential element of the reinforcement structure 22 may include one or more elastic segments 40, depending on the particular expansion characteristics desired.

Segment 40 may comprise a separate component from the remaining portions of the reinforcement structure 22 or may be formed integrally therewith. For example, the segment 40 may comprise a section of the circumferential element having a reduced cross-sectional area. Alternatively, the elastic segment 40 may comprise a separate component, such as an elastic band connected between separated ends of each circumferential element.

As mentioned previously, the reinforcement structure 22 may be disposed in, on, or between polymer layers. Preferably, relative movement between the elastic segment 40 and the polymer layer or layers is permitted such that each individual circumferential element of the reinforcement structure 22 is permitted to increase in circumference thereby allowing the distal tip portion 18 to expand radially. Relative movement between the elastic segment 40 and adjacent polymer layer or layers may be accomplished by coating the reinforcement structure 22 or just the elastic segment 40 with a lubricious material prior to applying the polymer layer(s).

Refer now to FIGS. 5A and 5B, which illustrate detailed views of an alternative embodiment of the distal tip portion 18 of the catheter 10 illustrated in FIG. 1, shown in the collapsed position and the expanded position, respectively. Except as described herein, the alternative embodiment illustrated in FIGS. 5A and 5B is the same in form and function as the embodiment illustrated in FIGS. 4A and 4B. In this particular embodiment, a spring or slack portion 50 is provided in each circumferential element of the reinforcement structure 22. Spring 50 may have a spring constant equal to zero such that the spring 50 merely acts as slack in the circumferential element of the reinforcement structure 22. Alternatively, the spring 50 may have a spring constant other than zero and may be biased in the compressed or expanded position. If biased in the compressed position, the spring 50 will have a tendency to assist in the expansion of the distal tip portion 18. If biased in the expanded position, the spring 50 will have a tendency to assist in the collapse of the distal tip portion 18. Thus, the spring constant, and bias associated therewith, may be selected to actuate expansion of the distal tip portion 18 at different threshold pressures.

Spring 50 may be formed integrally with each circumferential element of the reinforcement structure 22 or may be provided as a separate component connected between separated ends of each circumferential element of the reinforcement structure 22. For example, the spring 50 may be formed by reducing the circumference of the distal tip portion 18. Reducing the circumference may be accomplished by reducing the outside diameter or tapering the distal tip portion 18 using heat and pressure. Alternatively, the spring 50 may comprise a stamped portion of each circumferential element of the reinforcement structure 22, wherein the stamp forms a zigzag pattern in the circumferential element of the coil. The zigzag pattern or other suitable geometry may alternatively be chemically etched or cut as with a laser into each circumferential element of the reinforcement structure 22.

Refer now to FIGS. 6A and 6B, which illustrate detailed views of another alternative embodiment of the distal tip portion 18 of the catheter 10 illustrated in FIG. 1, shown in the collapsed position and the expanded position, respectively. Except as described herein, the embodiment illustrated in FIGS. 6A and 6B is the same in form and function as the embodiment illustrated in FIGS. 5A and 5B. In this particular embodiment, the reinforcement structure 20 of the proximal shaft portion 14 and the distal shaft portion 16 comprises a plurality of interwoven coils, i.e., a braid. Similarly, the expandable reinforcement structure 22 of the distal tip portion 18 comprises a braid structure, wherein each circumferential element of each coil defining the braid structure 22 includes a spring element 60. Although shown overlapping, each spring element 60 preferably acts independently. Each spring element 60 is substantially the same as spring element 50, except that the spring constant and bias of spring element 60 may be modified proportional to the increase in number of individual spring elements 60.

If an intermediate flexible tube is used as the reinforcement structure 22, the flexible tube includes a plurality of circumferential elements comprising bands of material. The bands of material may be continuously and integrally formed with the tube, or may be discrete bands connected in series with spacers therebetween. The bands may be made of an elastomeric material with suitable dimensions such that the tube expands exponentially under pressure from the first diameter to an asymptote diameter corresponding to the desired second diameter.

In addition to expansion by pressure inside the lumen 30, the expandable distal tip portion 18 may be expanded by other suitable means, such as by physical contact or by thermal expansion. For example, the expandable tip portion 18 may be radially expanded by inserting a device through the lumen 30, wherein the device has an outside diameter larger than the inside diameter of the distal tip portion 18. The physical contact between the device inserted in to the lumen 30 and the inside surface of the distal tip portion 18 generates a normal force against the wall of the tip tending to expand the distal tip portion 18 in the radial direction. Alternatively, the reinforcement structure 22 in the distal tip 18 may be formed of a material responsive to energy (e.g., thermal or electrical), such as a shape memory metal or a shape memory polymer. Similarly, the polymer layer or layers surrounding the reinforcement structure 22 may also be formed of a shape memory polymer. Energy may then be applied to the distal tip portion 18 by any suitable energy source such as by an electrical power source, resistive heating, RF heating or the like of the reinforcement structure 22.

In use, catheter 10 is inserted into the patient's vascular system and navigated to the desired target site using conventional catheterization techniques. Once the distal portion 18 is adjacent the desired target site in the patient's vascular system, a fluid or other material, such as an embolic agent, may be injected into the lumen 30 of the catheter 10. The distal tip portion 18 is then expanded by the application of pressure or other means described previously. Fluid or other material is then delivered through the lumen 30 of the catheter 10 to the desire treatment site. As discussed previously, the material disposed in the lumen 30 of the catheter 10 contributes to the generation of pressure therein, particularly when the material (e.g., embolic material) encounters resistance to flow in the tapered distal portion of the distal tip 18.

Figure 7:
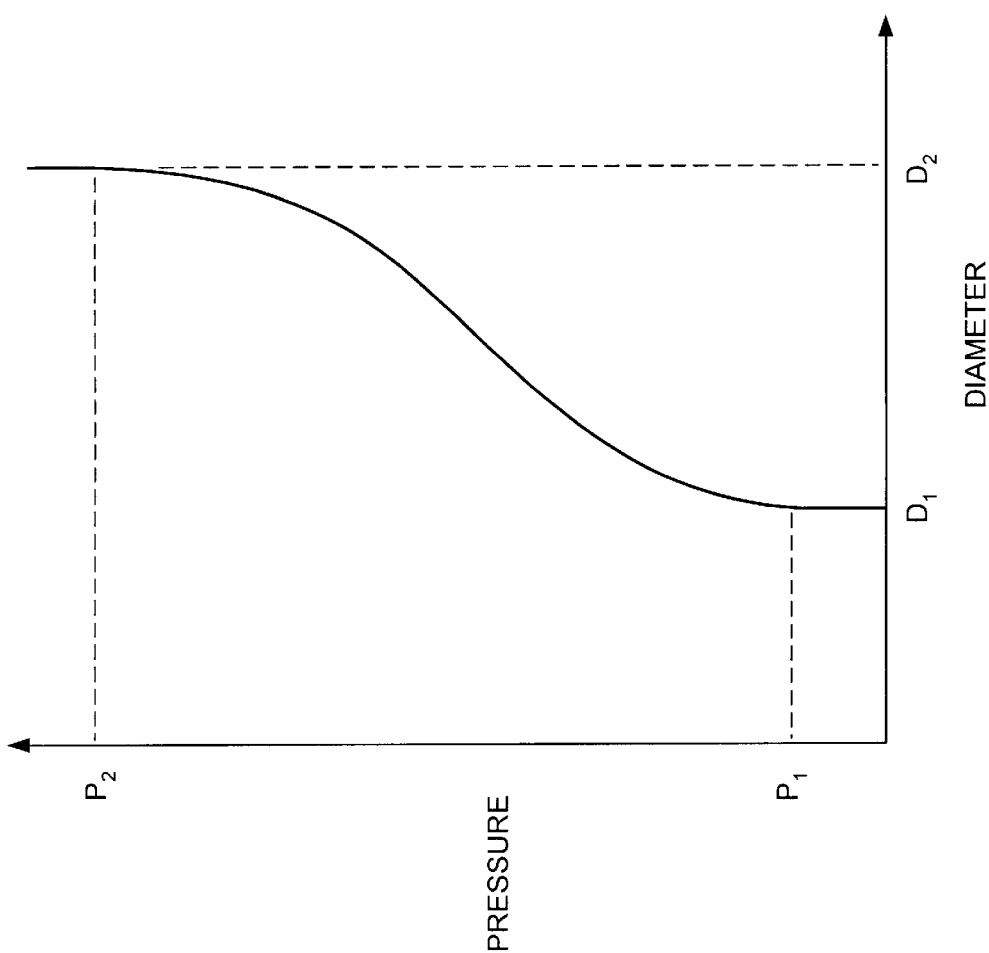
FIG. 7 is a graph illustrating controlled diametric expansion as a function of pressure of the various catheter embodiments.

Preferably, the distal tip portion 18 of the catheter 10 expands radially at a predictable rate with pressure as illustrated in FIG. 7. As can be appreciated from the graph illustrated in FIG. 7, the distal tip portion 18 maintains a first diameter $D_1$ below a first threshold pressure $P_1$. The distal tip portion 18 assumes a second diameter $D_2$ at a second threshold pressure $P_2$. The diameter change between $P_1$ and $P_2$ is predictable by the graph illustrated in FIG. 7. Above the second threshold pressure $P_2$, the second diameter $D_2$ is maintained constant. Preferably, $D_1$ is approximately 0.010 to 0.070 inches, and $D_2$ is approximately 0.012 to 0.080 inches. Also preferably, $P_1$ is approximately 0 to 50 psi, and $P_2$ is approximately 75 to 125 psi. The shape and limits of the pressure v. diameter graph may be altered by modifying the characteristics of the expansion means 40, 50 and 60 in the distal tip portion 18 and/or by modifying the polymer layer or layers in the distal tip portion 18. Those skilled in the art will recognize that many variables, including dimensions and material properties of the reinforcement layer 22, expansion means 40, 50 and 60, and polymer layers 34 and 36, contribute to the shape and limits of the pressure v. diameter curve. Because of the number of variables available to the catheter designer, conventional modeling techniques or empirical data may be used to craft the desired pressure v. diameter performance curve.

From the forgoing, it is apparent that the present invention overcomes disadvantages of prior art devices and methods by providing an intravascular catheter including a shaft having an expandable portion, preferably with a reinforcement structure. Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. An intravascular catheter comprising a reinforced circumferentially continuous tubular shaft having a lumen extending therethrough and an open distal end, the shaft including an expandable portion having a circumferentially continuous and radially expandable reinforcement structure, wherein the expandable portion is sufficiently expandable such that the shaft may expand from a first diameter to a second diameter upon increasing pressure in the lumen of the shaft.

2. An intravascular catheter as in claim 1, wherein the expandable portion is sufficiently elastic such that the shaft may return to the first diameter upon decreasing the pressure in the lumen of the shaft.

3. An intravascular catheter as in claim 1, wherein the expandable portion is disposed at a distal portion of the shaft.

4. An intravascular catheter as in claim 1, wherein the expandable portion is disposed at a distal tip of the shaft.

5. An intravascular catheter as in claim 4, wherein the reinforcement structure is disposed on a polymer tubular layer.

6. An intravascular catheter as in claim 4, wherein the reinforcement structure is disposed in a polymer tubular layer.

7. An intravascular catheter as in claim 4, wherein the reinforcement structure is disposed between two polymer tubular layers.

8. An intravascular catheter as in claim 7, wherein the reinforcement structure comprises a coil.

9. An intravascular catheter as in claim 7, wherein the reinforcement structure comprises a braid.

10. An intravascular catheter as in claim 7, wherein the reinforcement structure comprises a knit.

11. An intravascular catheter as in claim 7, wherein the reinforcement structure comprises an intermediate tube.

12. An intravascular catheter as in claim 3, wherein the reinforcement structure comprises a plurality of circumferential elements, each circumferential element having a circumference and a means for permitting an increase in the circumference such that the shaft may expand from the first diameter to the second diameter.

13. An intravascular catheter as in claim 12, wherein the reinforcement structure is disposed on a polymer layer, and wherein relative movement is permitted between the circumference increasing means and the polymer layer.

14. An intravascular catheter as in claim 12, wherein the reinforcement structure is disposed in a polymer layer, and wherein relative movement is permitted between the circumference increasing means and the polymer layer.

15. An intravascular catheter as in claim 12, wherein the reinforcement structure is disposed between polymer layers, and wherein relative movement is permitted between the circumference increasing means and the polymer layers.

16. An intravascular catheter as in claim 12, wherein the circumference increasing means comprises slack in the circumferential element.

17. An intravascular catheter as in claim 12, wherein the circumference increasing means comprises a spring in the circumferential element.

18. An intravascular catheter as in claim 12, wherein the circumference increasing means comprises an elastic segment in the circumferential element.

19. An intravascular catheter as in claim 18, wherein the elastic segment and the reinforcement structure are formed of the same material.

20. An intravascular catheter as in claim 19, wherein the reinforcement structure comprises a polymeric material.

21. An intravascular catheter as in claim 19, wherein the reinforcement structure comprises a metallic material.

22. An intravascular catheter as in claim 12, wherein the first diameter is maintained below a first threshold pressure.

23. An intravascular catheter as in claim 22, wherein the second diameter is established at a second threshold pressure.

24. An intravascular catheter as in claim 23, wherein the second diameter is maintained above the second threshold pressure.

25. An intravascular catheter as in claim 24, wherein the shaft expands predictably with pressure.

26. An intravascular catheter as in claim 25, wherein the first threshold pressure is between about 0 psi and about 50 psi.

27. An intravascular catheter as in claim 26, wherein the second threshold pressure is between about 75 psi and about 125 psi.

28. A method of delivering a therapeutic agent to a vascular site, comprising the steps of:

providing a catheter comprising a circumferentially continuous tubular shaft having a lumen extending therethrough and an open distal end, wherein a portion of the shaft includes a circumferentially continuous and radially expandable reinforcement structure that is sufficiently expandable such that the shaft may expand from a first diameter to a second diameter upon increasing the pressure in the lumen of the shaft;

navigating the catheter, at the first diameter, to the vascular site;

applying pressure to the lumen of the shaft thereby expanding the expandable portion of the shaft from the first diameter to the second diameter; and delivering the therapeutic agent to the vascular site through the lumen of the catheter, at the second diameter.

29. A therapeutic agent delivery method as in claim 28, wherein the therapeutic agent is disposed in the lumen of the shaft and the pressure is created, in part, by resistance of the therapeutic agent to flow through the lumen.

30. A therapeutic agent delivery method as in claim 28, wherein the reinforcement structure comprises a plurality of circumferential elements, each circumferential element having a circumference and a means for permitting an increase in the circumference such that the shaft may expand from the first diameter to the second diameter. the circumference such that the shaft may expand from the first diameter to the second diameter.

31. A therapeutic agent delivery method as in claim 30, wherein the shaft expands predictably with pressure.

32. A therapeutic agent delivery method as in claim 31, wherein the first diameter is maintained below a first threshold pressure.

33. A therapeutic agent delivery method as in claim 32, wherein the second diameter is established at a second threshold pressure.

34. A therapeutic agent delivery method as in claim 33, wherein the second diameter is maintained above the second threshold pressure.

35. A therapeutic agent delivery method as in claim 34, wherein the first threshold pressure is between about 0 psi and about 50 psi.

36. A therapeutic agent delivery method as in claim 35, wherein the second threshold pressure is between about 75 psi and about 125 psi.

* * * * *